United States Patent [19]

Müller

[11] 4,018,593
[45] Apr. 19, 1977

[54] PROCESS FOR RECOVERING USEFUL SUBSTANCES FROM CULTURE MEDIA

[76] Inventor: Hans Müller, Im Allmendli, 8703 Erlenbach, Switzerland

[22] Filed: June 19, 1975

[21] Appl. No.: 588,472

Related U.S. Application Data

[63] Continuation-in-part of Ser. No. 584,020, June 4, 1975.

[30] Foreign Application Priority Data

June 7, 1974 Switzerland ............... 7469/74
Apr. 9, 1975 Switzerland ............... 4600/75
June 21, 1974 Switzerland ............... 8653/74

[52] U.S. Cl. ........................ 71/76; 71/77;
71/79; 71/65; 195/49; 195/82; 195/66 R
[51] Int. Cl.² ............................ A01N 5/00
[58] Field of Search ............ 195/28 R, 114, 115,
195/100, 82, DIG. 9, 96, 49, 65, 66 R;
260/112 R; 47/1.4, DIG. 5; 71/77, 79, 65, 76;
210/2, 11

[56] References Cited

UNITED STATES PATENTS

| | | | |
|---|---|---|---|
| 3,520,777 | 7/1970 | Filosa | 195/28 R |
| 3,551,297 | 12/1970 | Hosler | 195/28 R X |
| 3,642,578 | 2/1972 | Hitzman et al. | 195/28 R |

OTHER PUBLICATIONS

Robbins "Thiamin and Plant Growth" Science vol. 89 1939 pp. 303-307.
Micheals "New Separation Technique for the CPI" Chemical Engineering Progress vol. 64 Dec. 1968 pp. 31-43.

*Primary Examiner*—R. B. Penland
*Attorney, Agent, or Firm*—Michael J. Striker

[57] ABSTRACT

A microorganism is cultivated with a liquid-containing culture medium so as to obtain a protein-containing cellular product. The latter is then recovered from the culture medium. Thereafter, the liquid portion of the culture medium is treated so as to obtain a first fraction which contains proteins and a second fraction which is substantially free of proteins and contains an active substance or active substances. The treatment of the liquid portion of the culture medium may include ultrafiltration, filtration through a molecular sieve, precipitation or solvent extraction. The active substances present in the second fraction may include growth factors and growth inhibitors for the microorganism. Certain of these growth factors and growth inhibitors are useful in the cultivation of green plants and the second fraction may be utilized for this purpose. On the other hand, all or part of the second fraction may be recycled for use in the cultivation of the microorganism. Aside from the recovery of active substances which is achieved by separating the liquid portion of the culture medium into first and second fractions, there is achieved the result that water pollution due to discharge of the culture medium may be reduced since the biochemical oxygen demand of the culture medium is decreased by removal of the proteins therefrom, that is, by recovering the protein content of the culture medium as a separate fraction.

12 Claims, No Drawings

PROCESS FOR RECOVERING USEFUL SUBSTANCES FROM CULTURE MEDIA

CROSS-REFERENCE TO RELATED APPLICATION:

This is a continuation-in-part of copending application Ser. No. 584,020 filed June 4, 1975 and entitled "Processes for the Production of Dry Proteinrich Nutriments by Cultivation of Microorganisms".

BACKGROUND OF THE INVENTION:

The invention relates generally to processes involving the cultivation of microorganisms. Of particular interest to the invention are processes for the cultivation of nutrient unicellular proteins.

Microorganisms such as yeasts, bacteria and fungi are today being cultivated in large quantities so as to produce protein-rich substances. The proteins obtained from microorganisms of this type are unicellular proteins and are given the designation "single cell proteins" (SCP).

The culture medium for the cultivation of the microorganisms requires a source of carbon. For this purpose, it is known to use carbohydrates, paraffins or paraffin hydrocarbons, alcohols and other substances which are rich in carbon.

There are many problems which must be taken into account for such cultivations. For instance, a number of other substances such as phosphates or phosphorus, nitrogen, potassium, calcium, magnesium and trace elements which participate in the synthesis of the cells must be added to the carbon source. Similarly, certain organisms require the addition of working substances such as biotin and yeast extract among others.

It is known that, subsequent to recovery of the microorganisms from the culture medium, a portion of the waste water or used culture medium may be recycled for use in the fermentation or cultivation. However, it has been found that this recirculation can be carried out to a certain point only. The reason is that, aside from the unused salts and working substances present in the used culture medium, the used culture medium also contains proteins, and particularly enzymes, which have been formed therein and which can no longer be utilized by the single cells. In fact, the proteins which have been formed in the used culture medium may even have a growth-inhibiting effect. Accordingly, recirculation of the used culture medium with all of its associated components for use in the cultivation cannot be carried out beyond a certain point.

Since recirculation of the used cultured medium is possible to a certain point only, a portion of the used culture medium must be discharged as waste. However, the quantities of the above-indicated substances present in the used culture medium pose great problems as regards water pollution. In particular, it has been found that the biochemical oxygen demand (BOD), which is a measure of the polluting ability, may reach values of several thousand milligrams per liter.

SUMMARY OF THE INVENTION

A general object of the invention is to provide a novel process wherein microorganisms are cultivated.

Another object of the invention is to provide a process wherein microorganisms are cultivated an which enables lesser water pollution than heretofore to be achieved.

A further object of the invention is to provide a process wherein microorganisms are cultivated and which enables improvements in economy to be realized.

An additional object of the invention is to provide a process which enables proteins, as well as other useful substances, to be recovered from the used culture media derived from the cultivation of microorganisms.

The foregoing objects, as well as others which will become apparent hereinafter, are achieved in accordance with the invention. According to one aspect of the invention, there is provided a process for recovering useful substances from culture media wherein a microorganism is cultivated with a liquid-containing culture medium so as to obtain a protein-containing cellular product. The product is recovered from the culture medium. The liquid portion of the culture medium is treated so as to obtain a first protein-containing fraction and a second fraction which is substantially free of proteins and contains an active substance.

The invention is based on the recognition that the total liquid portion or liquid of a used culture medium contains not only interesting, usable enzymes and other proteins but also contains substantial quantities of growth factors and growth inhibitors for the microorganism among others.

DESCRIPTION OF THE PREFERRED EMBODIMENTS:

As indicated previously, of particular interest to the invention are processes wherein nutrient, unicellular proteins are cultivated. Hence, the description herein will be primarily with reference thereto.

The cultivation of nutrient, unicellular proteins is known per se. For details of a process by which nutrient, unicellular proteins may be cultivated, reference may be had to applicant's copending application Ser. No. 584,020 filed June 4, 1975 and entitled "Processes for the Production of Dry Protein-rich Nutriments by Cultivation of Microorganisms". It will be understood, however, that the invention also has application to the used liquid culture media derived from other, conventional cultivation processes for nutrient, unicellular proteins.

An important object of the invention is the provision of a method for simultaneous recovery of proteins and active substances from used liquid portions of culture media. For the purposes of the present description and the appended claims, the term "active substance" will be construed to be distinct from the proteins present in the used liquid portion of a culture medium and to encompass the growth factors and growth inhibitors for the microorganism or microorganisms cultivated with the culture medium and which are present in the used liquid portion of the culture medium.

In accordance with one feature of the invention, the used liquid portion of a culture medium is subjected to a separation into protein-containing and substantially protein-free fractions. A fraction which is substantially free of proteins includes an active substance or active substances. By separating out the proteins and enzymes, the biochemical oxygen demand of the remainder of the used liquid portion of the culture medium may be reduced.

According to one embodiment of the invention, a fraction which is substantially free of proteins may be returned to the fermentation or cultivation apparatus, that is, may be recirculated for use in the fermentation or cultivation, in its entirety. In accordance with another embodiment of the invention, a fraction which is substantially free of proteins is only partially recirculated for use in the fermentation or cultivation.

Growth experiments have been carried out on the above-indicated fractions of the used liquid portions of culture media. These have shown that suitable processing of the growth factors and/or growth inhibitors, or of the protein-free fraction or fractions containing the same, is not only of great commercial value but concomitantly helps to reduce the problems associated with the used liquid portions of culture media and to make possible the handling of the used liquid portions of culture media in an economical manner.

Certain of the growth factors and growth inhibitors microorganisms are playing an every-increasing role in the cultivation of green plants, e.g. corn. It is possible to isolate or recover such a growth factor, or such growth factors, froma protein-free fraction containing the same. Similarly, it is possible to isolate or recover such a growth inhibitor, or such growth inhibitors, from a protein-free fraction containing the same. For a protein-free fraction containing a growth factor of the type under consideration, as well as a growth inhibitor of the type under consideration, both the growth factor and the growth inhibitor may be isolated or recovered from the fraction. On the other hand, a protein-free fraction which contains either a growth factor of the type under consideration or a growth inhibitor of the type under consideration, or both such a growth factor and such a growth inhibitor, may be directly used in the cultivation of green plants without isolating the growth factor and/or the growth inhibitor. However, it may be necessary to subject the fraction to an appropriate treatment prior to its utilization in the cultivation of green plants.

In general, growth factors and/or growth inhibitors of the type which may find application in the cultivation of green plants may be isolated in or as additional fractions if desired or necessary.

Aside from the growth factors and growth inhibitors which may find an application in the cultivation of the green plants, it is further possible to isolate or recover substances such as, for example, biotin, which are required in the process itself, that is, which are required in the fermentation or cultivation of the microorganism or microorganisms. In other words, a protein-free fraction may contain a substance which is, or substances which are, utilizable in the cultivation of microorganisms. Such a substance, or such substances, may also be isolated in or as an additional fraction or additional fractions. This is true whether or not the protein-free fraction contains growth factors and/or growth inhibitors useful in the cultivation of green plants in addition to the substance or substances which are usable in the cultivation of microorganisms. Such an additional fraction containing one or more substances utilizable in the cultivation of microorganisms may advantageously be recycled for use in the process, that is, the cultivation of the microorganism or microorganisms. Favorably, this additional fraction is recycled together with the dissolved salts.

The protein content and, above all, the enzymes, present in the used liquid portion of the culture medium may be removed from this liquid portion in various ways.

According to one embodiment of the invention, the treatment for removal of the proteins from the used liquid portion of the culture medium involves the precipitation of the protein content. Preferably, the precipitation is carried out at a number of different pH values.

Another embodiment of the invention contemplates the use of solvent extraction in order to recover the protein content of the used liquid portion of the culture medium.

In accordance with a further embodiment of the invention, the recovery of the protein content of the used liquid portion of the culture medium involves filtration through a membrane (ultrafiltration).

Still another embodiment of the invention contemplates the recovery of the protein content of the used liquid portion of the culture medium using filtration through a molecular sieve, e.g. zoelites.

By using the above separation procedures, it becomes possible to directly concentrate the protein content of the used liquid portion of the culture medium and, if desired, to subsequently dry the protein content. By separating out the proteins and enzymes, the biochemical oxygen demand of the used liquid portion of the culture medium may be reduced by up to about 90 percent.

The substances remaining in the filtrate or the substantially protein-free used liquid portion of the culture medium may, in turn, be separated or recovered by fractionation or extraction. These substances include the growth factors and growth inhibitors which are useful in the cultivation of green plants and the substances which are usable in the cultivation of the microorganism or microorganisms. In the event that the substances remaining in the substantially protein-free used liquid portion of the culture medium are separated by fractionation or extraction, part of the resulting fractions may be recycled for use in the cultivation of the microorganism or microorganisms.

The following Example describes a test which was performed in order to provide an illustration of the utility of the invention. It will be understood that this Example is presented so as to further illustrate the invention and is not intended to limit the same in any manner:

A specific yeast genus, namely, Hansenulla polymorpha, is continuously fermented on a solid substrate. A solution containing 10 percent by volume of methanol is added as a source of carbon. A cell suspension containing 24 grams per liter of yeast, calculated as dry matter, is obtained. After separating the yeast by means of a centrifuge, the cell-free, separated solution is subjected to ultrafiltration. The ultrafilter used is a Westinghouse module having a membrane which, according to the manufacturer's specifications, does not permit the passage of substances having a molecular weight in excess of 1000.

The permeate obtained is diluted with water to different degrees. This is set forth in the following Table:

| Permeate | Water |
|---|---|
| 100 | 0 |
| 90 | 10 |
| 80 | 20 |
| 70 | 30 |
| 60 | 40 |
| 50 | 50 |
| 40 | 60 |
| 30 | 70 |
| 20 | 80 |
| 10 | 90 |

-continued

| Permeate | Water |
| --- | --- |
| 0 | 100 |

Beakers of the tall type having a capacity of 200 milliliters are each halfway filled with a loose bed of glass wool. Glass tubes having an inner diameter of 5 millimeters are then inserted in the glass wool in such a manner that each tube extends to the upper rim of the respective beaker. The glass tubes subsequently serve for the introduction of the fluid to be tested into the beakers. The glass wool is covered with a filter paper and subsequently coated with a layer of quartz sand having a height of about 5 centimeters.

In each beaker, five kernels of corn are planted in the quartz sand in such a manner that they are just covered by the sand. Thereafter, 50 milliliters of each of the solutions set forth in the Table is introduced into a respective one of the beakers through the glass filling tubes.

The lengths of the sprouting corn plants are measured daily and an average value is assigned to each beaker.

From these experiments it was found that, for the case of the non-diluted used culture medium (100 percent permeate), as well as for the cases where the used culture medium had concentrations of 90 percent (90 percent permeate) and 80 percent (80 percent permeate), the growth was retarded or germination was actually prevented. For concentrations of the used culture medium below 70 percent (below 70 percent permeate), an acceleration in growth was observed which, for these experiments, reached a maximum at concentrations of the used culture medium of 20 and 30 percent (20 and 30 percent permeate). The plants cultivated with the latter exhibited an increase in length which exceeded that of the control groups cultivated with normal tap water by 20 to 30 percent.

It will be understood that each of the elements described above, or two or more together, may also find a useful application in other types of processes differing from the types described above.

While the invention has been illustrated and described as embodied in a process for the recovery of useful substances from the used culture media derived from the cultivation of unicellular proteins, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for recovering at least one member of the group consisting of proteins, enzymes, growth inhibitors, growth factors and other substances which are usable in the cultivations of microorganisms from culture media, comprising cultivating a microorganism in a liquid-containing culture medium so as to obtain a protein-containing cellular product; recovering said product from said culture medium; treating the liquid portion of said culture medium so as to obtain a first protein-containing fraction and a second fraction which is substantially free of protein and contains a growth inhibitor for said microorganism which is useful in the cultivation of green plants; and recovering said growth inhibitor from said second fraction.

2. A process as defined in claim 1, wherein said cultivation is carried out so as to produce nutrient unicellular proteins.

3. A process as defined in claim 1, wherein said treatment to recover protein comprises ultrafiltration.

4. A process as defined in claim 1, wherein said treatment to recover protein comprises filtration through a molecular sieve.

5. A process as defined in claim 1, wherein said treatment to recover protein comprises precipitation.

6. A process as defined in claim 5, wherein said precipitation is carried out at a plurality of pH values.

7. A process as defined in claim 1, wherein said treatment to recover protein comprises solvent extraction.

8. A process as defined in claim 1, wherein a portion of said second fraction is recycled for use in said cultivation.

9. A process as defined in claim 1, said second fraction being capable of accelerating the growth of plants when mixed with a quantity of water such that said second fraction is present in concentrations below a predetermined level; and wherein said second fraction is mixed with said quantity of water.

10. A process as defined in claim 1, wherein said cultivation comprises the fermentation of a yeast and said second fraction is capable of accelerating the growth of corn when mixed with said quantity of water.

11. A process as defined in claim 1, said second fraction being capable of accelerating the growth of plants when said second fraction is present in concentrations below about 70 percent of the total volume of liquid; and wherein said second fraction is mixed with a quantity of water such that the concentration of said second fraction is below about 70 percent of the total volume of liquid.

12. A process as defined in claim 11, wherein said second fraction is mixed with a quantity of water such that the concentration of said second fraction is between about 20 and 30 percent of the total volume of liquid.

* * * * *